United States Patent [19]

Vicario-Arcos

[11] Patent Number: 4,568,546
[45] Date of Patent: Feb. 4, 1986

[54] ANTIVENOM COMPOSITION

[76] Inventor: Timoteo Vicario-Arcos, Oriente 160 No. 1815, Col. Escuadrón 201, Z.P. 13, Mexico

[21] Appl. No.: 498,145

[22] Filed: May 25, 1983

[51] Int. Cl.$^4$ ............................................. A61K 35/78
[52] U.S. Cl. ................................................. 424/195.1
[58] Field of Search ............................ 424/195, 195.1

[56] References Cited

PUBLICATIONS

Poffer's Cyclopedia of Botanical Drugs and Preparations, 1950, pp. 301, 302, 349.

Primary Examiner—Albert T. Meyers
Assistant Examiner—John W. Rollins, Jr.
Attorney, Agent, or Firm—Fleit, Jacobson, Cohn & Price

[57] ABSTRACT

A composition effective against the symptoms of venom, such as convulsions and throat blockage, suffered by a victim of a venomous creature, which composition comprises an ethyl alcohol infusion of previously dried herbs and iron filings, said alcohol infusion being a supernatant decanted from an infusion of from 28 to 31 liters of an ethyl alcohol and water solution containing at least 55% ethyl alcohol; from 130 to 300 grams of red cinchona; from 130 to 300 grams of curcuma root; from 60 to 100 grams of aloe; from 80 to 200 grams of saffron; from 80 to 200 grams of white agaric; from 80 to 200 grams of nutmeg; from 250 to 400 grams manna; from 150 to 330 grams of gencian; from 70 to 170 grams of orange blossom; from 80 to 200 grams of rhubarb; from 450 to 650 grams of cinnamon; and from 2,800 to 3,500 grams of iron filings. The composition is prepared by mixing together the dried herbs and iron filings; submerging the mixture in from 28 to 31 liters of the ethyl alcohol solution; allowing the submerged mixture to stand for a period of time sufficient to form the infusion, preferably about 15 days; and decanting the supernatant from said mixture. The symptoms of venom may be effectively treated by orally administering to the victim a dosage unit consisting of one-half glass of water into which is mixed one spoonful of the composition.

6 Claims, No Drawings

ANTIVENOM COMPOSITION

FIELD OF THE INVENTION

The present invention refers to an antivenom composition and, more particularly, to an antivenom composition useful as antidote against the bite of venomous animals and which has proven to be also useful as an aid for healing burns and ulcers both on the skin and on the mucosa of the human body.

BACKGROUND OF THE INVENTION

Several vaccines for systemic or parenteral application are known in the prior art to prevent fatalities when a person has suffered the bite of a venomous animal such as snakes, scorpions and the like, but these vaccines are mainly in the form of serum, that is, mainly contain serum from animal which is highly toxic to certain persons who suffer from allergy against the antibodies contained by the serum used in said vaccines, such as horse serum.

Therefore, the field of application of said vaccines, has been considerably restricted in view of the fact that certain persons do not accept the serum contained in the vaccines and some times they die, if not of the venom injected by the animal, by the allergic shock caused by the vaccine itself.

Therefore, for long there has been the need of an antivenom composition, which by its nature itself and by its manner of application, will not cause allergic shocks and will nevertheless be highly effective against the venom of said animals.

OBJECTS OF THE INVENTION

Having in mind the defects of the prior art antivenom compositions, it is an object of the present invention to provide an antivenom composition which will not cause any allergic shock and yet will be highly effective against the venom of various animals.

It is one other object of the present invention to provide an antivenom composition, of the above mentioned character, which will be of a strictly vegetable origin in order to avoid the existence of any toxins which may cause secondary reactions in the victim.

It is still another object of the present invention to provide an antivenom composition of the above mentioned nature, which will be capable of being administered through the oral route and still so will be rapidly assimilatable in order to carry out its action against the poison of venomous animals.

The foregoing objects and others ancillary thereto are preferably accomplished as follows:

According to a preferred embodiment of the present invention, an antivenom composition, which has proven to be highly useful as antidote against the bite of venomous animals, and has also proven to be useful as an aid for healing burns and ulcers, is prepared by infusing, in ethyl alcohol, a mixture of red cinchona, curcuma root, aloes, saffron, white agaric, nutmeg, manna, gencian, orange blossom, rhubarb and cinnamon, together with an amount of iron filings.

The infusion is prepared by introducing the above mixture of herbs, previously dried, and iron filings, into a sufficient amount of 55% ethyl alcohol during about 15 days, and then filtering or decanting the solution to obtain the necessary infusion to be used as an antidote.

The novel features that are considered characteristic of the present invention are set forth with particularity in the appended claims. The invention itself, however, both as to its organization and its method of operation, together with additional objects and advantages thereof, will best be understood from the following detailed description of certain specific embodiments thereof.

DETAILED DESCRIPTION

The antivenom composition of the present invention comprises an ethyl alcohol infusion of 130 to 300 grams of red cinchona, 130 to 300 grams of curcuma root, 60 to 100 grams of aloes, 80 to 200 grams of saffron, 80 to 200 grams of white agaric, 80 to 200 grams of nutmeg, 250 to 400 grams of manna, 150 to 330 grams of gencian, 70 to 170 grams of orange blossom, 80 to 200 grams of rhubarb, 450 to 650 grams of cinnamon, and 2800 to 3500 grams of iron filings, in an amount of from 28 to 31 liters of ethyl alcohol.

The composition of the present invention is prepared by the steps of drying the above mentioned herbs, mixing said herbs together with the specified amounts of iron filings, and completely submerging the herbs and iron filings in the specified amount of ethyl alcohol, letting the thus obtained mixture to stand for about 15 days and either decanting or, filtering the supernatant infusion to be used as an antidote for the poison of venomous animals.

In accordance with a highly preferred embodiment of the invention, the antivenom composition of the present invention is obtained by infusing, in 29 liters of 55% ethyl alcohol, 220 grams of red cinchona, 200 grams of curcuma root, 80 grams of aloes, 140 grams of saffron, 140 grams of white agaric, 140 grams of nutmeg, 340 grams of manna, 280 grams of gencian, 120 grams of orange blossom, 140 grams of rhubarb, 560 grams of cinnamon and 3200 grams of iron filings.

The above alcoholic infusion of herbs and iron filings has been found to be absolutely effective against the poison of venomous animals, i.e., creatures, such as snakes, (for instance, rattlesnakes), scorpions, spiders, vesps and bees and also the said composition has been found to be highly effective as an aid for healing burns and ulcers either on the skin or on the mucosa of the human body.

The present invention will be more fully understood by means of the following examples which are given as illustrative but not as limitative of the present invention.

EXAMPLE 1

An antivenom composition was prepared by drying and mixing 220 grams of red cinchona, 220 grams of curcuma root, 80 grams of aloes, 140 grams of saffron, 140 grams of white agaric, 140 grams of nutmeg, 340 grams of manna, 280 grams of gencian, 120 grams of orange blossom, 140 grams of rhubarb, 560 grams of cinnamon and 3200 grams of iron filings, and infusing said mixture in 29 liters of 55% ethyl alcohol by allowing the mixture to stand during 15 days and then decanting the supernatant infusion.

A number of 45 persons were treated at different times with a dosage unit of the above mentioned composition, prepared by dissolving one spoonful of said infusion in one half glass of water, and administering said dosage unit to said persons who had suffered from the bite of venomous animals at different times. The above group of persons suffered from the bite of venomous animals as follows: 15 persons suffered from the bite of rattlesnake, 10 persons suffered from the bite of venomous scorpions, 10 persons suffered from the bite of vesps, 5 more persons suffered from the bite of venomous ants and 5 more suffered from the bite of bees.

To each one of said persons, at different times, namely, when the casualities occurred, the above dosage unit of the infusion of the present invention was administered orally, with which the symptoms of the action of the venom injected by the venomous animals practically disappeared in a complete manner within a few hours. When a considerable time elapsed for certain ones of the victims from the moment of the bite to the time of the treatment and said victims started to suffer from convulsions or throat blocking, the said dosage unit was applied by using warm water, with which the symptoms of the action of the poison also practically disappeared. In some cases it was necessary to administer a second dosage unit of the infusion of the present invention to obtain complete disappearance of the symptoms of the action of the poison.

EXAMPLE 2

A group of 10 persons suffering from different types of burns on the skin was selected, and by using the infusion prepared as described in Example 1, said infusion was directly applied to the skin five times per day the first five days and then reducing the number of applications by one per day, until the burns were healed by the end of approximately the tenth day.

EXAMPLE 3

A group of patients suffering from different types of ulcers on the mucosas of the gastrointestinal tract was selected, and an oral dosage unit of two spoonfuls of the infusion prepared in accordance with Example 1, without dilution, was administered orally to said patients, twice a day before taking meals, with which the ulcers were healed in approximately from 15 to 20 days.

Although certain specific embodiments of the present invention have been shown and described, it is to be understood that certain modifications thereof are possible. The present invention, therefore, is not to be restricted except insofar as is necessitated by the prior art and by the spirit of the appended claims.

What is claimed is:

1. A composition effective against the convulsions and throat blockage symptoms of venom suffered by a victim of a venomous creature, which composition comprises an ethyl alcohol infusion of previously dried herbs and iron filings, said alcohol infusion being a supernatant decanted from an infusion of
   from 28 to 31 liters of an ethyl alcohol and water solution containing at least 55% ethyl alcohol;
   from 130 to 300 grams of red cinchona;
   from 130 to 300 grams of curcuma root;
   from 60 to 100 grams of aloe;
   from 80 to 200 grams of saffron;
   from 80 to 200 grams of white agaric;
   from 80 to 200 grams of nutmeg;
   from 250 to 400 grams manna;
   from 150 to 330 grams of gencian;
   from 70 to 170 grams of orange blossom;
   from 80 to 200 grams of rhubarb;
   from 450 to 650 grams of cinnamon; and
   from 2,800 to 3,500 grams of iron filings.

2. A composition according to claim 1, wherein said supernatant is decanted from an infusion of
   29 liters of an ethyl alcohol and water solution containing 55% of ethyl alcohol;
   220 grams of red cinchona;
   220 grams of curcuma root;
   80 grams of aloe;
   140 grams of saffron;
   140 grams of white agaric;
   140 grams of nutmeg;
   340 grams of manna;
   280 grams of gencian;
   120 grams of orange blossom;
   140 grams of rhubarb;
   560 grams of cinnamon; and
   3,200 grams of iron filings.

3. A method of preparing a composition effective against the convulsions and throat blockage symptoms of venom, suffered by a victim of a venomous creature, which composition comprises an ethyl alcohol infusion of previously dried herbs and iron filings, said alcohol infusion being a supernatant decanted from an infusion, said method comprising:
   a. mixing together dried herbs and iron filings in the following amounts:
      from 130 to 300 grams of red cinchona;
      from 130 to 300 grams of curcuma root;
      from 60 to 100 grams of aloe;
      from 80 to 200 grams of saffron; from 80 to 200 grams of white agaric;
      from 80 to 200 grams of nutmeg;
      from 250 to 400 grams manna;
      from 150 to 330 grams of gencian;
      from 70 to 170 grams of orange blossom;
      from 80 to 200 grams of rhubarb;
      from 450 to 650 grams of cinnamon; and
      from 2,800 to 3,500 grams of iron filings;
   b. submerging the herbs and iron filings mixture in from 28 to 31 liters of an ethyl alcohol and water solution containing at least 55% of ethyl alcohol;
   c. allowing the submerged mixture to stand for a period of time of about fifteen days; and
   d. decanting said supernatant from said mixture.

4. A method according to claim 3, wherein dried herbs and iron filings are mixed together in the following amounts:
   220 grams of red cinchona;
   220 grams of curcuma root;
   80 grams of aloe;
   140 grams of saffron;
   140 grams of white agaric;
   140 grams of nutmeg;
   340 grams of manna;
   280 grams of gencian;
   120 grams of orange blossom;
   140 grams of rhubarb;
   560 grams of cinnamon; and
   3,200 grams of iron filings.

5. A method for effectively treating the convulsions and throat blockage symptoms of venom, suffered by a victim of a venomous creature, said method comprising:
   orally administering to the victim a dosage unit consisting of one-half glass of water into which is mixed one spoonful of a composition effective against the symptoms of venom, which composition comprises an ethyl alcohol infusion of previously dried herbs and iron filings, said alcohol infusion being a supernatant decanted from an infusion of from 28 to 31 liters of an ethyl alcohol and water solution containing at least 55% ethyl alcohol;
from 130 to 300 grams of red cinchona;
from 130 to 300 grams of curcuma root;
from 60 to 100 grams of aloe;
from 80 to 200 grams of saffron;
from 80 to 200 grams of white agaric;
from 80 to 200 grams of nutmeg;
from 250 to 400 grams manna;
from 150 to 330 grams of gencian;
from 70 to 170 grams of orange blossom;
from 80 to 200 grams of rhubarb;
from 450 to 650 grams of cinnamon; and
from 2,800 to 3,500 grams of iron filings.

6. A method according to claim 5, wherein said supernatant is decanted from an infusion of
29 liters of an ethyl alcohol and water solution containing 55% of ethyl alcohol;
220 grams of red cinchona;
220 grams of curcuma root;
80 grams of aloe;
140 grams of saffron;
140 grams of white agaric;
140 grams of nutmeg;
340 grams of manna;
280 grams of gencian;
120 grams of orange blossom;
140 grams of rhubarb;
560 grams of cinnamon; and
3,200 grams of iron filings.

* * * * *